United States Patent [19]
Palmacci

[11] Patent Number: 4,976,262
[45] Date of Patent: Dec. 11, 1990

[54] ICE BAG HOLDING DEVICE

[76] Inventor: Jed Palmacci, 9005 South 3605 East, Sandy, Utah 84093

[21] Appl. No.: 303,439

[22] Filed: Jan. 27, 1989

[51] Int. Cl.$^5$ ............................. A61F 7/08; A61F 7/10
[52] U.S. Cl. ..................................... 128/402; 128/382; 383/901
[58] Field of Search ............... 128/400, 402, 403, 379, 128/380, 382; 383/901; 62/259, 3, 530

[56] References Cited

U.S. PATENT DOCUMENTS

| | | |
|---|---|---|
| 1,169,123 | 1/1916 | Bams .................................. 128/380 |
| 3,491,761 | 1/1970 | Baker .................................. 128/402 |
| 3,889,684 | 6/1975 | Lebold ................................ 128/402 |
| 4,055,188 | 10/1977 | Pelton .................................. 128/402 |
| 4,527,566 | 7/1985 | Abare .................................. 128/402 |
| 4,585,003 | 4/1986 | Meistrell ............................. 128/402 |

FOREIGN PATENT DOCUMENTS 2548536  1/1985  France ................................. 128/402

OTHER PUBLICATIONS

Body Glove—Orthopedic Equipment—Promotional Literature

Primary Examiner—Edward M. Coven
Assistant Examiner—Mark S. Graham
Attorney, Agent, or Firm—Lynn G. Foster

[57] ABSTRACT

A novel ice or other temperature-imposing bag holder or retainer that is securely, adjustably, compressively and releasably placed around an injured joint. The presently preferred holders or retainers comprise stretchable material with good elastic memory comprising a pocket or pouch. During use, for example, a bag of ice or some other contained subambient cooling substance is placed within the pocket or pouch and against an injured joint and the entire retainer is stretch-wrapped around an injured joint under tension counter to the memory of the holder or retainer such that the cooled substance is gently and securely applied to the injury for prevention or minimization of swelling. Velcro fastening strips hold the retainer in its stretched wrapped condition upon the injured joint.

7 Claims, 5 Drawing Sheets

ICE BAG HOLDING DEVICE

FIELD OF INVENTION

The present invention relates generally to the treatment of bodily injuries and more specifically to devices whereby the application of a low temperature substance to an injured joint is securely, comfortably and reliably facilitated.

PRIOR ART

Application of ice or some other cooling agent, whether chemically or physically prepared, is a common treatment for damaged joints. For example, when an athlete injures a knee or some other joint during the course of athletic competition, a bag of ice is typically promptly applied thereto to prevent swelling. When the injured athlete must be moved to a different location for further treatment, a problem is encountered in attempting to secure the ice bag to the injured joint for the transportation process.

One often-used method of securing the cooling source to the injured joint entails manually holding it in place with one or both hands. This can represent a difficulty to the one designated as holder since it is not always possible to transport the injured person in a manner or position in which the injured joint remains immobile. The motion of the joint caused by transportation and the possibly awkward pOsition of the joint during transportation combine to make this method of securing the cooling source unsatisfactory. Furthermore, there is not always a third party available to function as a holder. When the injured party functions as a bolder, the pain associated with the injury is often increased as well as the overall discomfort.

Another common technique of attaching a cooling source to an injured joint comprises wrapping or lashing the bag or other container in which the cooling source is contained to the joint with an elastic wrap or similar wrap-type material. While this method may be more effective than that just mentioned, it has several disadvantages. Movement of the joint caused by transportation often causes the securing wrap to loosen or unravel. Movement of the ice pack or the like in respect to the injured joint, because the wrap is too loose or becomes loose, aggravates the injury and increases pain. If the wrap has been wound too tightly around the injured joint or if any discomfort caused by the wrap ensues, it is time-consuming and tedious to make adjustments by completely unwinding and then rewinding the wrap. More importantly, the level of pain in the injured joint is increased when the wrap is too tight. Finally, leakage caused by melting of the ice or the like will soak the wrap and create an unsightly mess.

As typified in U.S. Pat. No. 4,585,003, it has been that wet suit material be die-cut to present an aperture (through which a spout of an ice or like pack is extended) and pairs of opposed legs which are wrapped about a joint and velcro-like secured. This prior art proposal is limited to wet suit material lined with Neoprene which does not breathe, irritates, causing rashes and the like and accommodates bacterial infestation and growth thereof which contaminates the user's skin. Further more, this prior art proposal does not provide external access to the ice pack and does not provide internal confinement for the ice pack.

BRIEF SUMMARY AND OBJECTS OF THE INVENTION

In brief summary, the present invention overcomes or substantially alleviates the cited prior art problems by providing a novel ice or similar coolant or temperature-imposing bag holder or retainer that is securely, adjustably, compressively and releasably placed around an injured joint. The presently preferred holders or retainers comprise a flat stretchable material with good elastic memory which comprises a pocket or pouch, which both externally and internally constrains the ice pack against undesired migration. The retainers breathe, do not irritate or cause rashes and do not accommodate bacterial or like infestation and growth which is readily transferred to the user. During use, a bag or flexible envelope of ice or some other contained cooling substance is placed within the pocket or pouch and against the injured joint. The retainer is stretch wrapped in both directions around the injured joint under manual tension counter to the memory of the holder or retainer. Thus, the subambient temperature of the coolant within the envelope is gently and securely applied for prevention or minimization of swelling. Velcro fastening strips or the like may be used to hold the retainer in its oppositely wrapped condition upon the injured joint. The pocket which contains the ice bag or the like in one preferred embodiment is externally accessed to by flaps which are opened and closed by Velcro fastening strips or the like. The ice bag or the like may comprise an exposed spout and lid through which the ice or other cooling substance is initially displaced. Water from the melted ice may be drained through the spout and the ice bag refilled without removing the ice bag from the pocket and without removing the bag holder from the injured joint.

With the foregoing in mind, it is a primary object of the present invention to provide a holder or retainer for a coolant or temperature-imposing bag and related methods.

It is a further paramount object to provide a holder or retainer for an envelope containing a material having a subambient or superambient temperature wherein the holder or retainer is comprised of a strong stretchable breathable sheet material with good elastic memory which is facilely and releasably oppositely secured to an injured joint holding the envelope against the injured site and asserting just the proper pressure thereon.

Another dominant object is the provision of a holder or retainer for a temperature-imposing pack or bag which does not irritate or cause rashes and does not accommodate bacterial or like infestation and growth and transfer of said bacteria to the user.

Another important object is the provision of an ice or other temperature-imposing bag holder or retainer which may be securely and releasably placed oppositely around an injured joint and which will remain securely fastened thereto during movement and during transportation of the injured person to another location.

A further object of primary importance is the provision of a retainer for a temperature-imposing pack or bag which provides a pocket which retains the bag both internally and externally and/or concerning which external access is readily available.

An additional significant object is to provide a novel ice bag holder or retainer and related methods having one or more of the features and advantages: lightweight, noncomplex, effective, inexpensive, safe, utilizes few parts, easy to use, strong and convenient.

These and other objects and features of the present invention will be apparent from the detailed description taken with reference to the accompanying drawings.

DETAILED DESCRIPTION OF THE ILLUSTRATED EMBODIMENT

Figure 7:
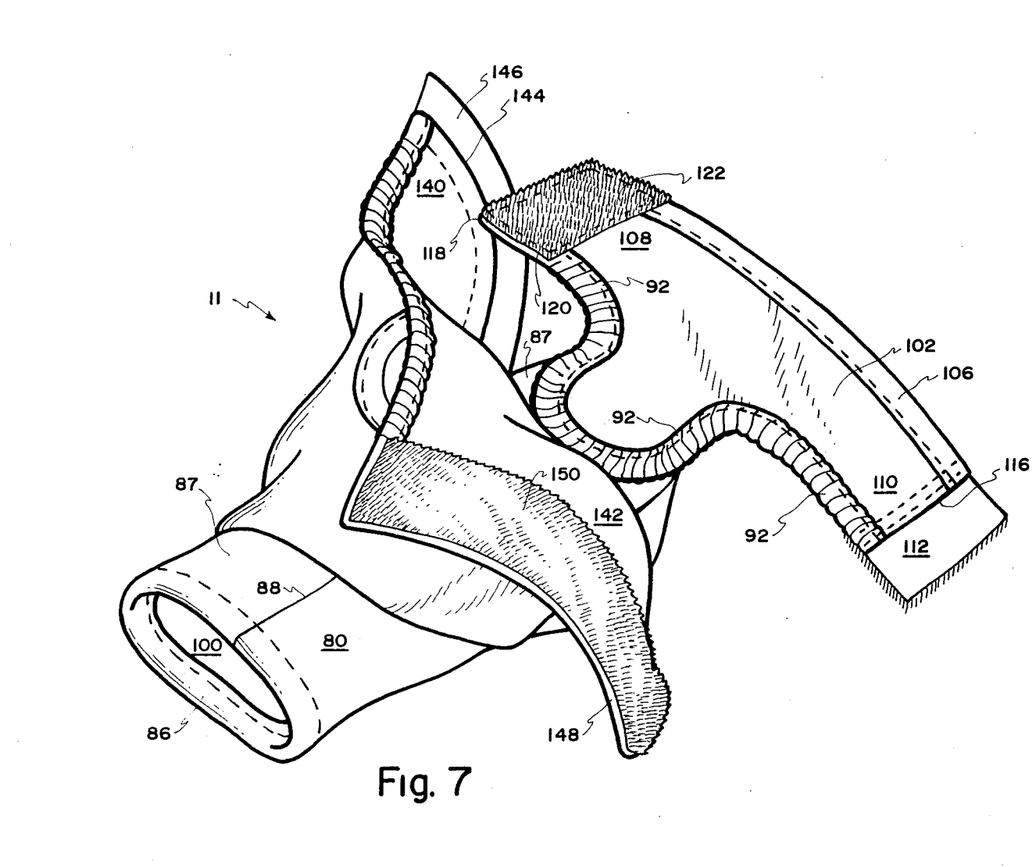
FIG. 7 is a perspective view of the ice bag holder of FIG. 5 in an open, partially unfolded condition.
Figure 8:
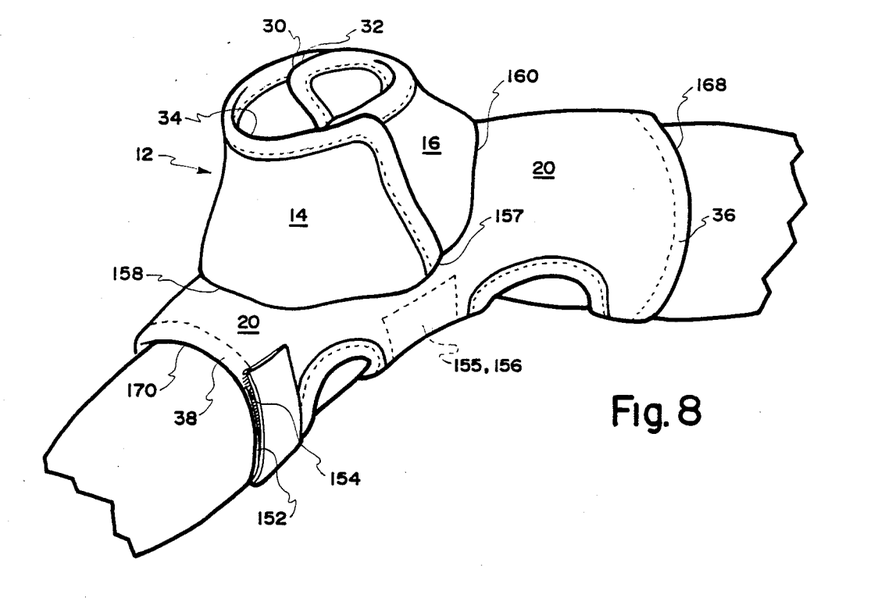
FIG. 8 is a perspective view of a further preferred embodiment for use on an elbow shown in its "as used" stressed position.
Figure 9:
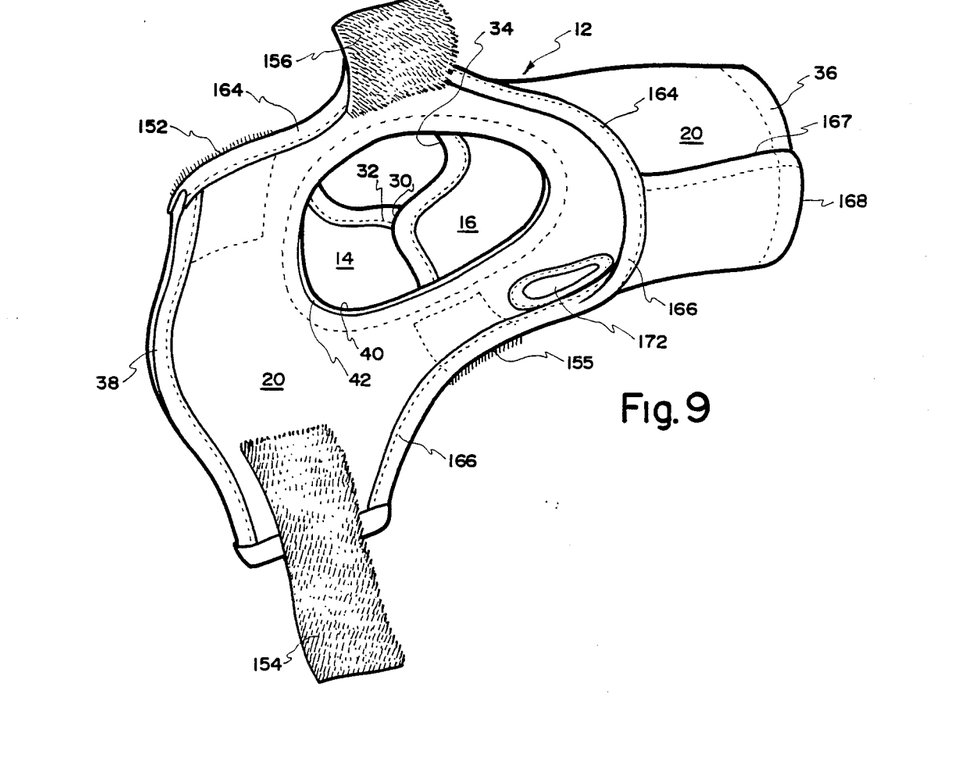
FIG. 9 is a perspective view of the embodiment of FIG. 8 shown in a detached, unfolded condition.
Figure 10:
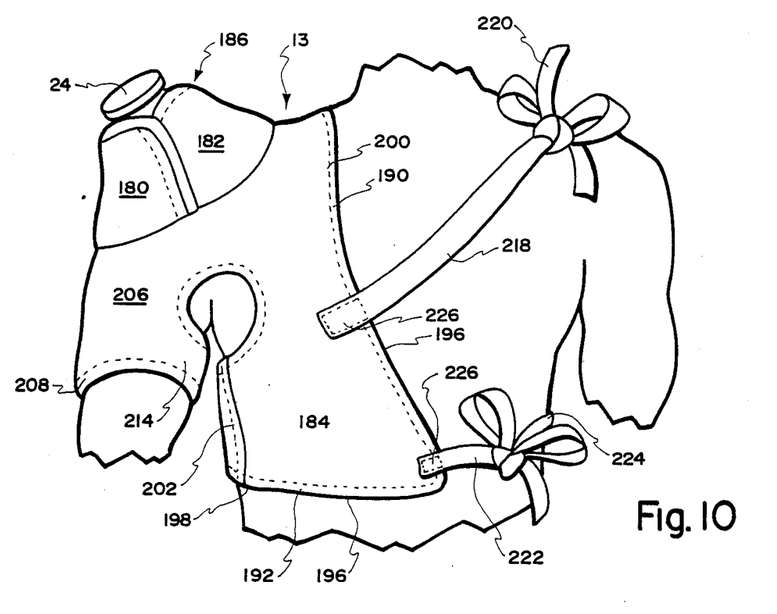
FIG. 10 is a perspective view of still a further preferred embodiment for use on a shoulder shown in its "as used" stressed position.
Figure 11:
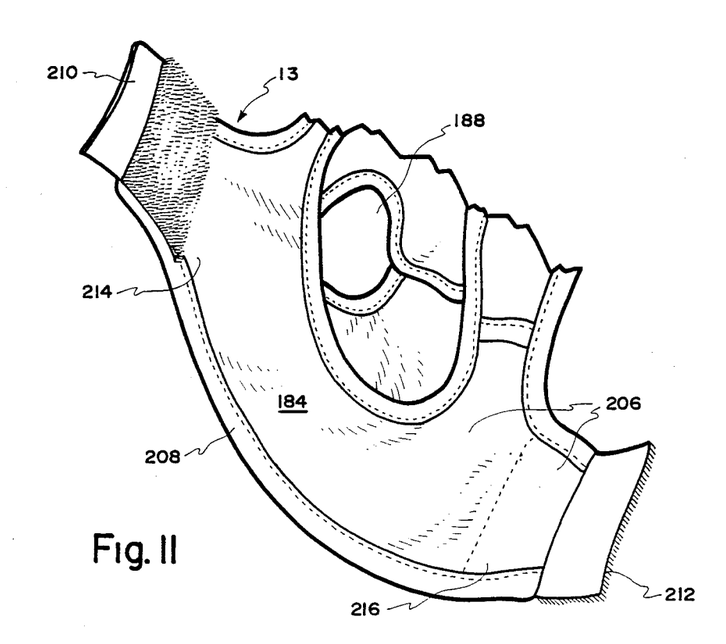
FIG. 11 is a fragmentary perspective view of the embodiment of FIG. 10 shown in a detailed, unfolded condition.

Reference is now made to the drawings, wherein like numerals are used to designate like parts throughout. A presently preferred knee ice bag holding device, generally designated 10, is illustrated in FIGS. 1–4. A second presently preferred ankle ice bag holding device, generally designated 11, is illustrated in FIGS. 5–7. A third presently preferred elbow ice bag holding device, generally designated 12, is shown in FIGS. 8–9, and a fourth presently preferred shoulder ice bag holder, generally designated 13, is shown in FIGS. 10–11. Each holder or retainer 10, 11, 12 and 13 is hereinafter described in detail.

The holding device, holder or retainer 10 is specifically designed for use around the knee of the user and is primarily fabricated from three pieces of stretchable sheet material and stitched (sewn) appropriately together in combination with certain releasable fastening devices such as Velcro, as hereinafter more fully explained. The preferred sheet material is a fabric sold under the name Super Stretch and available from Associated Fabrics located in New York, N.Y. Holder 10 is, more specifically, formed, as presently preferred, from three strips of stretchable sheet material 14, 16 and 20. A hollow accessible compartment or pocket 22 (FIG. 3) is formed between the sheet segments 14 and 16, on the one hand, and sheet segment 20, on the other hand. Compartment 22 is sized, shaped and located to receive a specifically shaped flexible ice bag, the cap 24 of which is exposed in FIG. 1.

The holder or retainer 10 comprises opposed matching end Velcro fasteners 26 and 28, adapted to releasibly interlock, as hereinafter more fully explained. The holder or retainer 10 also comprises interlocking centrally overlapping Velcro strips 30 and 32 interposed between sheet segments 14 and 16 on opposite sides of the central opening 34. As can be seen from FIG. 3, sheet 20 is essentially a rectangular piece comprising opposed sides edges 36 and 38, which are generally disposed in spaced parallel relation one to another, and a centrally disposed circular aperture defined by circular edge 40. Edge 40 is covered by a U-shaped edge material 42, extending through the full 360 degrees of the aperture formed by edge 40. All edging material disclosed herein has substantial elasticity so that it will stretch and return to an unstressed state with the stretchable sheet material. Preferably, the edging material comprises Lycra, available from Associated Fabrics.

The edge material 42 is appropriately stitched to the material forming sheet 20 adjacent the edge 40. Preferably the diameter formed by the edge 40 is of such a size that a conventional ice pack of flexible design filled with ice can be initially collapsed, inserted through the opening formed by edge 40 and edging material 42 and thereafter flattened so as to have a diameter substantially greater than the diameter formed by edge 40. Thus, sheet 20 holds the ice pack in the pocket 22 during use. Aperture at 40 also accommodates direct contact between a surface of the ice pack and the injured site at the knee of the user.

Figures 1, 2, 3:
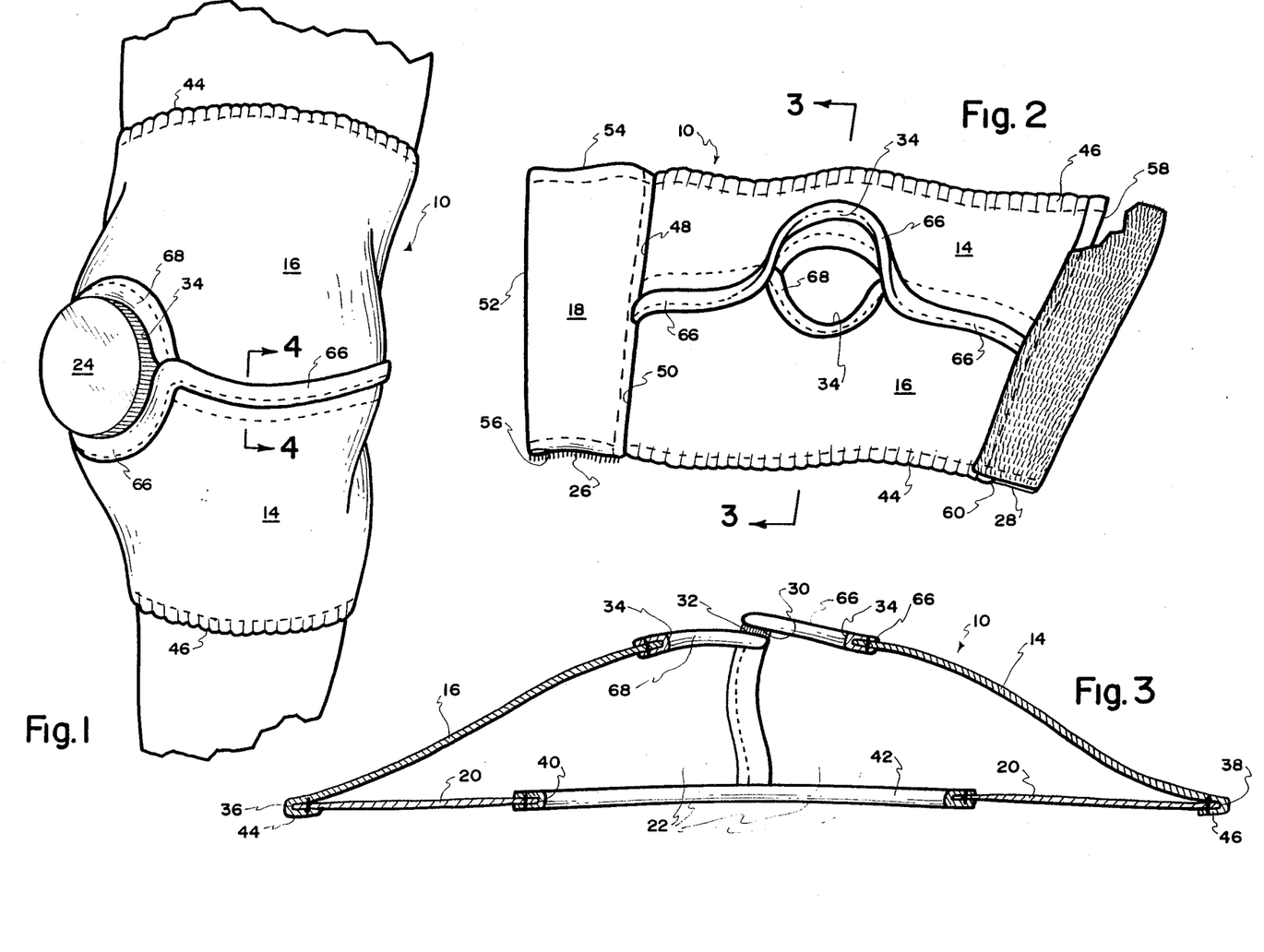
FIG. 1 is a front perspective view of a presently preferred subambient coolant holder, according to the present invention, shown in an "as used" stressed position on an injured knee, with an ice bag carried therein having an exposed spout and removable cap.
FIG. 2 is a perspective view of the ice bag holder of FIG. 1 in its detached linearly open unstressed position with the ice bag removed.
FIG. 3 is an enlarged cross-section taken along the lines 3—3 of FIG. 2.

In a side-to-side direction, edges 36 and 38 are gathered and stitched respectively to gathered contiguous edges of the sheet section 16 and 14, respectively. More specifically, sheet edge 44 of sheet section 16, while gathered, is folded over the gathered edge 36, the two edges are stitched together in the gathered condition so as to form the dome shape necessary to produce pocket 22, as shown in FIGS. 2 and 3. Similarly, the edge 46 of sheet section 14 is gathered and folded over the gathered edge 38 of sheet section 20. The edges 38 and 46 are thereafter stitched to unite the same in the described gathered relationship.

As best seen in FIG. 2, sheet sections 14 and 16 terminate along a common interface, i.e. at folded over edges 48 and 50. The folded over edges 48 and 50 are concealed between the sheets 14 and 16 and the sheet 20. Sheet 20 extends from the interior of the retainer or holder 10 to the exterior thereof at edges 48 and 50. Flap site 18 (FIG. 2) is, thus, an exposed extension of sheet 20. The extension 18 of sheet 20 comprises a folded over edge 52, which edge is interposed between the underside of extension 18 and the previously mentioned rectangular strip of Velcro fastener 26. The Velcro fastener 26 and the extension 18 at edge 52 are securely stitched together. Likewise, the extension 18 and the Velcro fastener strip 26 are stitched to each other adjacent edges 54 and 56 and adjacent edges 48 and 50.

Sheets segments 14 and 16 terminate in aligned side edges 58 and 60. See FIG. 2. A lap joint is formed by appropriate stitching between the Velcro fastening strip 28 and the sheet segments 14 and 16 adjacent edges 58 and 60, as illustrated in FIG. 2. While two continuous Velcro strips 26 and 28 are shown it is to be appreciated that each could be in two or more parts without departing from the scope of the invention. Also, 360° Velcro loops can be used to secure the configuration of FIGS.

1-3 and almost any of the configuration of the present invention.

Sheet segments 14 and 16 comprise centrally disposed overlapped transverse edges 62 and 64. See FIG. 4. Edge 62 is encased within a stretchable U-shaped edging strip 66, which is stitched to sheet 14 adjacent edge 62. Edge 64 is concealed with a U-shaped edging piece 68, which is stitched to sheet segment 16 adjacent edge 64. Two linearly spaced Velcro strips 30 are stitched to edge piece 66 and sheet 14, one between edge 48 and central aperture 34 and the other between central aperture 34 and edge 58. Similarly, two linearly spaced Velcro strips are stitched to edging strip 68 and sheet segment 16 along two locations, i.e. between edge 50 and central aperture 34 and between central aperture 34 and edge 60.

The diameter of aperture 34 is sized so that the spout and cap 24 of a conventional ice pack may be readily fitted therethrough. The velcro fastening strips 30 and 32, which releasibly hold the central edges 62 and 64 of sheet segments 14 and 16 into releasibly locked relationship on both sides of the aperture 34 may be forceably separated for the purpose of inserting or removing the entire ice pack, as desired. However, removal of the ice pack is not necessary if it is merely desired to remove melted ice contained therein. This water may be drained from the ice pack by removing cap 24 gravity draining the water from the ice pack. The ice pack may be refilled with a new supply of ice through the spout thereof prior to closing the spout with cap 24.

It should also be apparent that the ice pack can initially be placed within the pocket 22 of the holder or retainer 10 prior to placement of the holder or retainer around the injured knee. In the alternative, the holder or retainer 10 can be placed upon the knee and the ice pack inserted thereafter. It should further be appreciated that the location of the holder 10 and the ice pack therein can be anywhere around the entire 360° periphery of the knee, depending upon the location of the injury to the knee. The holder or retainer 10, in its open flattened state shown in FIG. 2, has a side-to-side dimension when unstressed, which is less then the circumference of the knee upon which it is intended to be placed. Accordingly, the user must oppositely wrap the retainer 10 around the knee, stretching the retainer 10 in the process and maintaining the stretched condition while the Velcro fasteners of strips 28 and 26 are secured together. Thus, in a preferred embodiment, the holder or retainer imposes a modest, predetermined compressive force upon &he injured joint. The compressive force may be adjusted by manually shifting the amount of overlap between Velcro strips 26 and 28.

The holding device, retainer or holder 11 is similar in principle to retainer 10, described above, but is specifically for use with an ankle joint. Materials from which retainer 11 is formed preferably are the same or equivalent to the materials heretofore described for use in fabricating retainer 10. Retainer or holder 11 comprises two pieces 80 and 82 of stretchable sheet material with memory. Sheet segments 80 and 82 are pre-cut blanks stitched into the substantially concentric relationship illustrated in FIGS. 5-7.

Holder or retainer 11 is illustrated in FIGS. 5 and 6 as being wrapped about an injured ankle 84 of a human being. The distal end of the sheet segment 80 is inwardly lapped upon itself to form edge 86 and stitched in said lapped condition, as best illustrated in FIGS. 6 and 7. Adjacent the distal edge 86, the sheet material at 87 is looped to bring two longitudinal edges together which are stitched to form seam 88. Tubular portion 87 is adopted to engage the user's instep 89 in compressive relation.

Stitched seam 88 extends from the distal edge 86 to a bifurcation in the sheet segment 80 at curvilinear edge site 90. Edge site 90 is disposed, as illustrated in FIGS. 5 and 6 adjacent the lower portion of the arch of the user's foot 84. Thus, the portion 87 of the holder 11 disposed between the arch and the toes of the user is generally tubular and divergently tapers slightly from edge 86 to edge 90. The edge 90 is generally curvilinear, preferably circular, extending through 180 degrees in each direction from seam 88, when the holder 11 is fully installed upon the ankle of the user, as illustrated in FIGS. 5 and 6. Edge 90 is concealed within a stretchable U-shaped edging piece 92, which is stitched to the sheet piece 80 adjacent the edge 90, as best illustrated in FIG. 6. The edge piece 90 thus provides a window 94 whereby one side of a conventional ice pack comprising cap 24 (FIG. 5) may be contiguously compressively placed against the arch and ankle of the user.

At each side of the heel site 96, an initial V-shaped notch in the sheet material 80 has been closed and stitched to itself along opposed seam lines 98. Each seam line 98 intersects the edge 90 and the edging piece 92 at or near the ankle of the user, as best illustrated in FIG. 6. The seams 98 cause a 90 degree turn at heal 96, turning the sheet 80 from the horizontal foot region 100 to the vertical region 102.

Region 102, when installed as illustrated in FIG. 6, is generally tubular, except for the opening defined by edging piece 92. The unstressed diameter of the vertically directed tubular portion 102 is less than the diameter of the leg of the user at site 104 so that the material forming the tubular portion 102 must be oppositely stretched around the leg portion of the user 104 for correct placement. Similarly, the tubular portion 87 has a transverse dimensional makeup which is smaller than the instepped area 89 of the foot 84 of the user so that it too must be slightly stretched and, consequently, exerts a modest predetermined compressive pressure upon the instep 89 of the user.

Tubular portion 102 of the sheet segment 80 comprises an upper edge 106, which is folded upon and stitched to itself, as illustrated in FIG. 6. The tubular portion 102 when opened into a flat configuration, shown in FIG. 7, comprises opposed flaps 108 and 110. Flap 110 has a Velcro strip 112 stitched thereto. The Velcro strip 112 comprises Velcro fasteners 114. Strip 112 extends beyond but partially overlaps the edge 116 of the flap 110.

The flap 108 comprises edge 118. A Velcro strip 120 comprising Velcro fasteners 122 is superimposed entirely over the flap 108 along the interior surface thereof.

Once the foot of the user is fitted through the instep collar region 87, the heal 96 is properly positioned and flaps 108 and 110 are oppositely wrapped around the leg portion 104 of the user above the ankle in stretched relation. The mating Velcro fasteners of strips 114 and 120 are caused to interlock so that the flaps 108 and 110 are secured together in the position illustrated in FIG. 6 and the tubular portion 108 exerts a modest predetermined compressive force upon the leg portion 104. The compressive force can be adjusted by varying the amount of overlap between strip 114 and 120.

It can be noted by observation of FIGS. 6 and 7 that the edge 90 is placed within the U-shaped edging member 92 in a gathered state so as to provide a substantial amount of elasticity along the edge, the edge material forming 92, as stated above, being elastic in nature as well. Thus, any ankle retainer of the type illustrated in FIGS. 5–7 will fit a plurality of foot and ankle sizes.

As mentioned before, ankle holder 11 comprises a second segment of sheet material 82. The lower edge 130 is folded upon itself and stitched in the folded condition across the top region of the instep portion 87 to sheet segment 82 from one heel seam 98 to the other. The front portion of the sheet segment 82 above the arch of the user has an aperture at circular edge 132 formed therein. Edge 132 is concealed within a U shaped elastic edging piece 132, which is stitched to the arch region of the sheet segment 82 adjacent the edge 132. The diameter of the aperture at edge piece 134 is sized so that the spout upon which the cap 24 of an ice pack of conventional design can be readily fitted therethrough.

The top of the sheet segment 82 is folded upon itself, to create a U-shaped upper lip 136 and is stitched to itself in the folded condition The edge 136 is illustrated as being disposed in the assembled condition (FIG. 6) at a location along the leg portion 104 of the user slightly above the edge 106. However, the reverse can be true or the edges 106 and 136 may be substantially superimposed, if desired, without departing from the scope of the present invention. The edge 136 is gathered prior to being stitched. The total length of the edge 136 is less than the circumference of the leg region 104. Thus, the edge 136 is stretched around the leg site 104 for installation. It can be appreciated from observation of FIG. 6 that concentric tubular portions of the holder 11 are placed upon the leg site 104. It can also be appreciated in its assembled condition, that the space between the sheet portion 80 and 82 adjacent the arch of the user comprise or form a pocket 138 in which a conventional flexible ice pack comprising cap 24 is positioned. The ice pack, in the preferred embodiment of FIGS. 5–7 is inserted into the pocket 138 prior to assembling the holder 11 upon the leg site 104.

As seen best in FIG. 7, in the open condition, the sheet segment 82 comprises opposed flaps 140 and 142. Flap 140 comprises edge 144, which is partially superimposed over a Velcro strip 146 in lap joint relation. The Velcro strip 146 is stitched to the flap 140 adjacent the edge 144, as best illustrated in FIG. 7. Velcro strips 146 and 150 can be replaced by spaced straps of opposed Velcro strips of 360° Velcro loops which attach to themselves.

Flap 142 comprises edge 148. A Velcro strip 150 is entirely superimposed upon flap 142 and stitched in position, as illustrated in FIG. 7. The vertical dimension of the flaps 140 and the strips 146 and 150 are such as lo extend from the edge 136 to a location slightly above the heel 96, when assembled. See FIG. 6. To secure the flaps 140 and 142 to the leg site 104, the user oppositely wraps the flaps 140 and 142 around the leg region 104 while stretching the flaps and causes the Velcro fasteners of strip 146 and 150 to engage each other. Thus, a modest predetermined amount of compressive force is exerted by the wound flaps 140 and 142 upon the leg region 104, which can be adjusted by varying the amount of overlap between strips 146 and 150.

When the flaps 108 and 110 and the flaps 140 and 142 are Velcro secured as illustrated in FIG. 6 around the foot, ankle and lower leg regions, the ice pack in pocket 138 contiguously, along one surface thereof will be compressively applied against the arch and ankle regions.

With reference to FIGS. 8 and 9, the holding device, holder or retainer 12 is specifically designed for use around the elbow of the user and is thus similar both in construction and principle to the device 10 previously described. Materials from which retainer 12 is formed preferably are the same or equivalent to the materials heretofore described for use in the fabricating of retainer 10. Since device 10 and device 12 comprise many identical or substantially identical components, many of the same numerals used to describe device 10 are repeated to describe device 12.

As with holder 10, holder 12 is more specifically formed, as presently preferred, from three strips of stretchable sheet material 14, 16 and 20. A hollow accessible compartment or pocket 22 (FIG. 8) is formed between the sheet segments 14 and 16 on the one hand and sheet segment 20 on the other hand. Compartment 22 is sized, shaped and located to receive a specifically shaped flexible ice bag. Holder or retainer 12 comprises two opposed matching end Velcro fasteners 152 and 154, and 155 and 156, adapted to releasibly interlock. The holder or retainer 12 also comprises interlocking centrally overlapping Velcro strips 30 and 32 interposed between sheet segments 14 and 16 on opposite sides of the central opening 34.

Sheet material 20 is essentially a rectangular piece comprising opposed side edges 36 and 38 and a centrally disposed circular aperture defined by circular edge 40. Edge 40 is covered by a U-shaped edge material 42, preferably Lycra and available from Associated Fabrics, extending through the full 360 degrees of the aperture formed by edge 40. Edge material 42 is appropriately stitched to the material forming sheet 20 adjacent the edge 40. As with knee device 10, the diameter formed by edge 40 is preferably of such a size that a conventional ice pack of flexible design filled with ice can be initially collapsed, inserted through the opening formed by edge 40 and edging material 42 and thereafter flattened so as to have a diameter substantially greater then the diameter formed by edge 40. Thus, sheet 20 holds the ice pack in the pocket 22 during use. The aperture at 40 also accommodates direct contact between a surface of the ice pack and the injured site at the elbow of the user.

Edges 36 and 38 are folded over upon each other and sewn so as to form a smooth edge. Pocket 22 is formed by stitching or sewing the bottom edges 158 and 160 of sheet segments 14 and 16 respectively in a circular manner to the sheet 20 such that the aperture formed by edge 40 is centered within the pocket 22.

Figure 4:
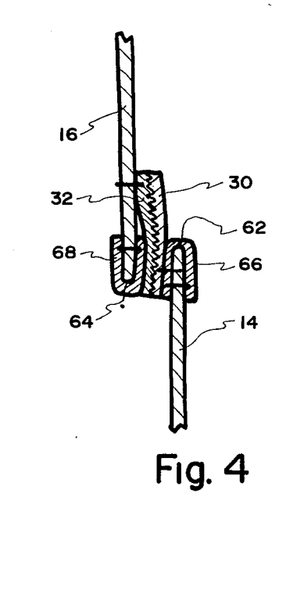
FIG. 4 is an enlarged cross-section taken along lines 4—4 of FIG. 1.
Figures 5, 6:
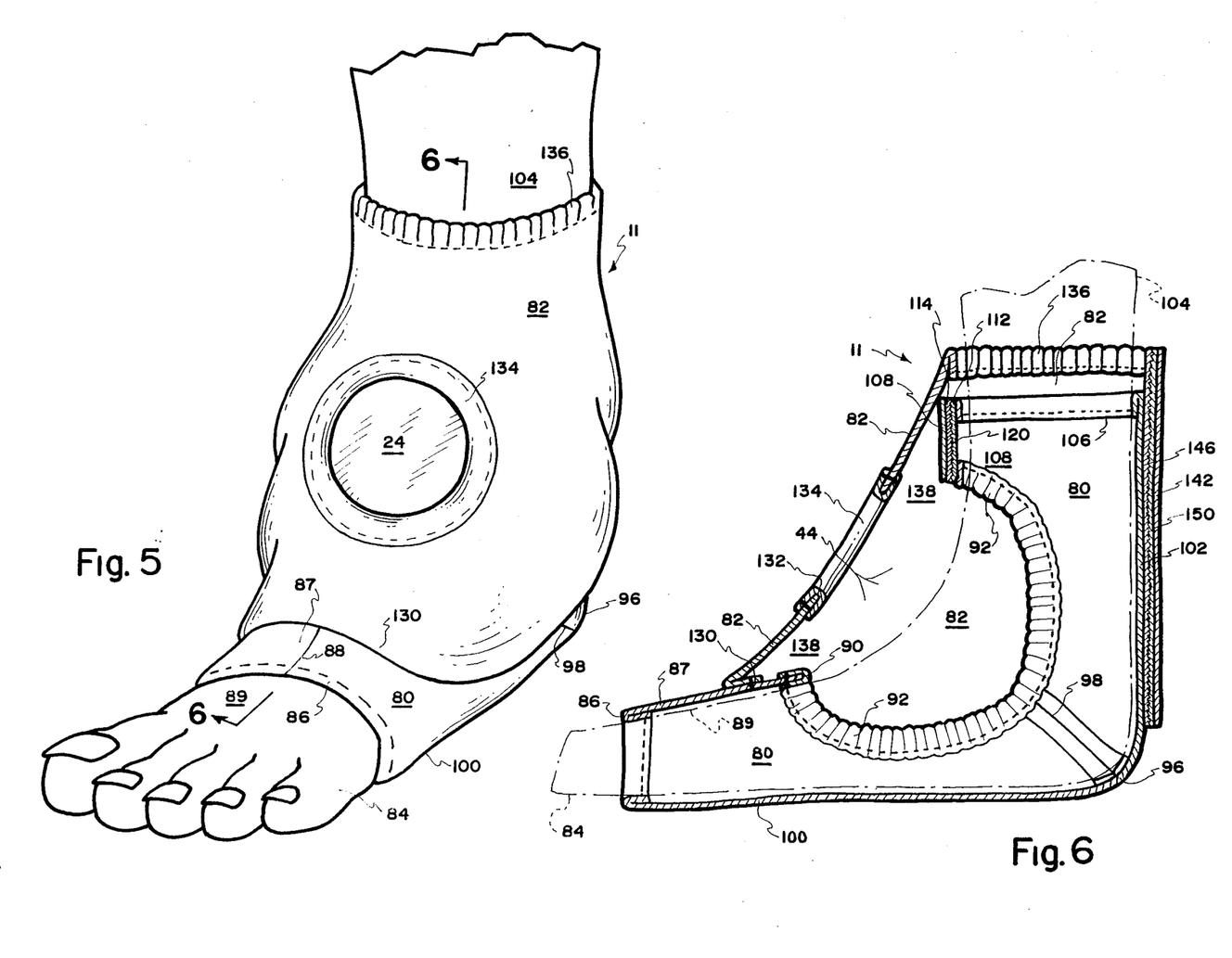
FIG. 5 is a front perspective view of another presently preferred ice bag holder, according to the present invention, shown in an "as used" position wrapped upon an injured ankle, with an ice bag carried therein having an exposed cap.
FIG. 6 is a cross-section taken along the lines 6—6 of FIG. 5, with the ice bag and ankle removed for clarity.

Segments 14 and 16 comprise centrally disposed overlapping transverse edges 62 and 64 as shown in FIG. 4. Edge 62 is encased within a stretchable U-shaped edging strip 66 which is stitched to sheet 14 adjacent edge 32. Edge 64 is concealed within the U-shaped edging piece 68 which is stitched to sheet segment 16 adjacent edge 64. Two sets of linearly spaced Velcro strips 30 and 32 are stitched to edge piece 66 and sheet 14, and to edge piece 68 and sheet 16 respectively; each set beginning on opposite sides of the central aperture 34 and running downwardly therefrom to form a junction 157 with edges 158 and 160.

The diameter of aperture 34 is sized so that the spout and cap 24 of a conventional ice pack may be readily fitted therethrough. The Velcro fastening strips 30 and 32, which releasibly hold the central edges 62 and 64 of sheet segments 14 and 16 into releasibly locked relationship of both sides of the aperture 34, may be forceably separated for the purpose of inserting or removing the entire ice pack as desired.

However, removal of the ice pack is not necessary if it is merely desired to remove melted ice contained therein. This water may be drained from the ice pack by removing cap 24 and gravity draining the water from the ice pack. The ice pack may be refilled with a new supply of ice through the spout thereof prior to closing the spout with cap 24.

It should also be apparent that the ice pack can initially be placed within the pocket 22 of holder or retainer 12 prior to placement of the holder or retainer around the injured elbow. In the alternative the holder or retainer 12 can be placed upon the elbow and the ice pack inserted thereafter.

Sheet segment 20 terminates in side edges 164 and 166, as best shown in FIG. 9. Edges 164 and 166 are brought together at one end and stitched appropriately at seam 167 so as to form circular aperture 168 defined by edge 36.

In use, the aperture 168 is slipped about the forearm of the user in positioning the device or holder 12. During use, edge 38 is also made to form an aperture 170. This is facilitated by use of Velcro straps 152 and 154 located on side edges 164 and 166 and at or near the edge 38. Thus, when in use, the device generally forms a tubular-shaped assembly about the arm which encloses the injured elbow.

A second Velcro strap arrangement 154 and 156 is similarly located at side edges 164 and 166, respectively, and midway between Velcro fasteners 152 and 154 and the adjoinment of side edges 164 and 166 at seam 167. The remainder of side edges 164 and 166 are indented between seam 167 and fasteners 154 and 156, and between fasteners 154 and 156 and fasteners 152 and 154. This facilitates movement of the injured joint and provides comfort to the user. All exposed areas of side edges 164 and 166 are covered by the same U-shaped edge material 42 that covers edge 40. Also, as presently preferred, a circular aperture 172 is cut or otherwise formed in sheet 20 between Velcro fastener 156 and edge 36 as shown in FIG. 9.

With reference to FIGS. 10 and 11, holder 13 is similar in principle to retainer 10 described above, but is specifically for use with the shoulder joint. Thus, the materials from which holder 13 is formed preferably are the same or equivalent to the materials heretofore described for use in fabricating retainer 10. Retainer or holder 13 comprises three pieces 180, 182 and 184 of stretchable sheet material with memory, and is illustrated in FIG. 10 as being wrapped about an injured shoulder of a human being. A hollow accessible compartment or pocket 186, best shown in FIG. 10, is formed between the sheet segments 180 and 182 on the one hand and sheet segment 184 on the other hand. Compartment 186 is sized and shaped and serves the same function as the compartment 22 previously described.

Segment 184 is form-fitted specifically for use with a human shoulder and comprises an aperture 188, end seams 190 and 192. Segment 184 is folded upon itself at edges 194 and 196 to create a U-shaped lip 198 and 200 and is stitched to itself in the folded condition. Sheet 184 is then looped to bring two longitudinal edges together which are stitched to form seams 202 and 204. Seam 202 creates the aperture 188 and seam 204 in connection with seam 202 creates an aperture through which the arm adjacent the injured shoulder may be situated.

Sheet 184 also comprises flap section 206 which drapes over the arm adjacent the injured shoulder. Flap 206 comprises edge 208 and Velcro Fasteners 210 and 212. Flap edge 208 is inwardly lapped upon itself and stitched in said lapped condition, as best illustrated in FIG. 11. Velcro fasteners 210 and 212 are attached at the ends of arms 214 and 216 which extend transversely from the major axis of flap 206. In use, the Velcro fasteners 210 and 212 are attached after wrapping the flap 206 about the upper arm adjacent to the injured shoulder of the user.

As best shown in FIG. 10, two sets of straps 218, 220 and 222, 224 facilitate secure attachment of the holder 13 to the torso of the injured party. The proximal end 226 of each strap 218, 220, 222, 224 is stitched or sewn appropriately to sheet segment 184. Straps 218 and 220 are drawn together and tied on the uninjured shoulder of the user. Straps 222 and 224 are drawn together and tied at the side of the waist opposite the injured shoulder.

As mentioned, aperture 188 is similar in virtually all respects to the aperture formed by the edge 40 and edging material 42 as described for the holder 10. Also, the compartment or pocket 186 is virtually identical in all respects to pocket 22 of elbow device 12. For this reason, identical numbers are used in describing various parts and components thereof.

By using velcro fasteners in the various embodiments of the present invention as illustrated and described, the pressure level applied to the injured joint may be adjusted either up or down as the need arises. It should also be apparent that embodiments of the present invention may be constructed in various sizes to meet all needs of humans and animals.

The invention may be embodied in other specific forms without department from the spirit or essential characteristics thereof. The present embodiments, are, therefore, to be considered in all respects as illustrative and not restrictive, the scope of the invention being indicated by the appended claims rather than by the foregoing description, and all changes which come within the meaning and range of equivalence of the claims are therefore to be embraced therein.

What is claimed and desired to be secured by United States Letters Patent is:

1. An ice bag holding device for an injured joint comprising:
   two way flexible wrap means comprising first flexible wall means to be contiguously wrapped in one direction upon an injured joint, second flexible wall means to be contiguously wrapped upon the injured joint in another direction and means by which the first and second wall means are releasibly secured together in their respective wrapped positions;
   yieldable protruding ice bag restraining means permanently carried by at least one of the wall means, the restraining means comprising flexible exterior layer means defining exposed frontal aperture means through which a spout of an ice bag may be caused to protrude and flexible interior layer means juxtaposed the exterior layer means, the interior layer means comprising interior aperture means greater in size than the exposed aperture means through which contiguous contact by the ice bag with the injured joint is achieved.

2. The device according to claim 1 wherein the wall means and the layer means comprise stretchable breathable material means with memory by which a predetermined amount of compression is applied to the injured joint.

3. The device according to claim 1 wherein the releasibly securing means comprise hook loop fasteners.

4. The device according to claim 1 wherein the releasibly securing means comprise tie strings.

5. The device according to claim 1 wherein the exterior layer means comprise at least two segments having openable fastener means therebetween whereby upon opening of the fastener means the size of the exposed aperture means is greatly enlarged permitting selective frontal removal and insertion of the ice bag without removal of the flexible wrap means from the injured joint.

6. The device according to claim 1 wherein the exterior layer means comprise at least two segments having openable fastener means therebetween upon opening of the fastener, means the size of the exposed frontal aperture means is greatly enlarged permitting selective frontal removal and insertion of the ice bag without substantial change in the compressive force applied to the injured joint by the flexible wrap means.

7. An ice bag holding device for an injured joint of a human being comprising:

two way flexible wrap means comprising first flexible wall means to be contiguously wrapped in one direction upon an injured joint, second flexible wall means to be contiguously wrapped upon the injured joint in another direction and means by which the first and second wall means are releasibly secured together in their respective wrapped positions;

yieldable protruding pouch forming ice bag restraining means permanently carried by at least one of the wall means, the restraining means comprising flexible exterior layer means defining exposed frontal aperture means, the aperture means comprising means by which the size of the aperture means can be manually enlarged and constricted whereby when enlarged the ice bag can be inserted into and removed from the pouch forming ice bag restraining means and when constricted a spout of the ice bag may protrude therethrough, the pouch forming ice bag restraining means further comprising flexible interior layer means juxtaposed the exterior layer means, the interior layer means comprising interior aperture means greater in size than the constricted exposed aperture means through which contiguous contact by the ice bag with the injured joint is achieved.

* * * * *